United States Patent [19]

Rothenberg et al.

[11] 4,410,706

[45] Oct. 18, 1983

[54] PREPARATION OF 2-VINYLIMIDAZOLES BY DEHYDROGENATION OF 2-ETHYLIMIDAZOLES AND 2-ETHYLIMIDAZOLINES

[75] Inventors: Alan S. Rothenberg, Norwalk; Hans P. Panzer, Stamford; Joseph L. Schmitt, Bethel; Roger J. Card, Stamford, all of Conn.

[73] Assignee: American Cyanamid Company, Stamford, Conn.

[21] Appl. No.: 379,608

[22] Filed: May 19, 1982

[51] Int. Cl.$^3$ ............................................ C07D 233/58
[52] U.S. Cl. ................................ 548/335; 548/346; 548/347
[58] Field of Search ................................ 548/335, 346

[56] References Cited

U.S. PATENT DOCUMENTS 4,340,744  7/1982  Schwarz et al. .

FOREIGN PATENT DOCUMENTS 703899  3/1941  Fed. Rep. of Germany ...... 548/335

OTHER PUBLICATIONS

Houben-Weyl, *Methoden der Organischen Chemie*, vol. V/16, Georg Thieme, Stuttgart, 1972, pp. 44–45.
Kirk-Othmer, *Encyclopedia of Chemical Technology*, 2nd Ed., Supplement vol., John Wiley, New York, 1971, pp. 653–655.

*Primary Examiner*—Richard A. Schwartz
*Attorney, Agent, or Firm*—Frank M. Van Riet

[57] ABSTRACT

A method for preparing 2-alkenylimidazoles from readily available 2-alkylimidazoles or 2-alkylimidazolines by dehydrogenating the 2-alkylimidazole or 2-alkylimidazoline in the presence of a suitable dehydrogenation catalyst. The preferred method provides 2-vinylimidazole by dehydrogenating 2-ethylimidazole or 2-ethylimidazoline. The reaction is advantageously carried out in a vapor phase in the presence of an inert carrier gas using as preferred dehydrogenation catalysts, copper chromites and catalysts comprising one or more of the metals molybdenum, iron, cobalt, zinc or chromium on non-reducible oxide supports such as alumina or silica.

9 Claims, No Drawings

PREPARATION OF 2-VINYLIMIDAZOLES BY DEHYDROGENATION OF 2-ETHYLIMIDAZOLES AND 2-ETHYLIMIDAZOLINES

BACKGROUND OF THE INVENTION

This invention relates to 2-alkenylimidazoles and, more particularly, to a method for preparing such 2-alkenylimidazoles.

Compositions based on 2-alkenylimidazole monomers which have been mono- or dialkylated or quaternized to provide salts and then homo- or copolymerized together or with other copolymerizable monomers find use in the treatment of aqueous particulate suspensions. For example, such polymeric compositions based on 2-vinylimidazole are effective to facilitate dewatering of aqueous suspensions of organic and inorganic materials in water and waste water treatments, mineral processing, paper manufacturing and the like.

Prior art methods for preparing 2-alkenylimidazoles largely require the use of starting materials which are not always easy to obtain. Thus, there exists a need for alternative methods for preparing 2-alkenylimidazoles.

SUMMARY OF THE INVENTION

The present invention enables 2-alkenylimidazoles to be prepared from readily available 2-alkylimidazoles or 2-alkylimidazolines without the need to resort to difficult to obtain starting materials. Such is achieved, according to this invention, by dehydrogenating the 2-alkylimidazole or 2-alkylimidazoline in the pressence of a suitable dehydrogenation catalyst to provide the 2-alkenylimidazole.

An object of this invention is the provision of a method for preparing 2-alkenylimidazoles from 2-alkylimidazoles or 2-alkylimidazolines.

The preferred method provides 2-vinylimidazole by dehydrogenating 2-ethylimidazole or 2-ethylimidazoline. The reaction is advantageously carried out in a vapor phase in the presence of an inert carrier gas using as preferred dehydrogenation catalysts, copper chromites and catalysts comprising of one or more of the metals molybdenum, iron, cobalt, zinc or chromium or non-reducible oxide supports such as alumina or silica.

A further object of this invention is the provision of a method for preparing 2-vinylimidazoles by dehydrogenating 2-ethylimidazoles or 2-ethylimidazolines in the presence of a dehydrogenation catalyst.

The foregoing and other objects, features and advantages of this invention will be further apparent from the following description of preferred embodiments thereof.

DESCRIPTION OF THE PREFERRED EMBODIMENTS

A 2-alkenylimidazole having the following structure:

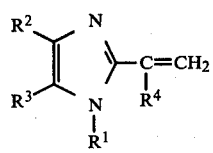

wherein $R^1$ is hydrogen or methyl, $R^2$ and $R^3$ are hydrogen, methyl or phenyl and $R^4$ is hydrogen or methyl, is prepared by dehydrogenating a 2-alkylimidazole (I) or a 2-alkylimidazoline (II) having the following structures:

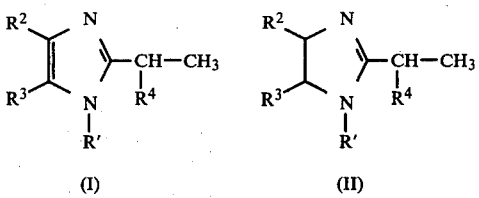

wherein $R^1$, $R^2$, $R^3$ and $R^4$ have the same significance as above.

Exemplary of the 2-alkylimidazoles useful as the starting material in the process of this invention are the following: 2-ethylimidazole, 2-isopropylimidazole, 1-methyl-2-ethylimidazole, 1-methyl-2-isopropylimidazole, 4,5-dimethyl-2-ethylimidazole, 4,5-diphenyl-2-ethylimidazole, 4(5)-methyl-2-ethylimidazole, 4(5)-methyl-2-isopropylimidazole.

Exemplary of useful 2-alkylimidazolines are: 2-ethylimidazoline, 2-isopropylimidazoline, 1-methyl-2-ethylimidazoline, 1-methyl-2-isopropylimidazoline, 4,5-dimethyl-2-ethylimidazoline. Dehydrogenation of the foregoing according to the process of this invention will yield the following exemplary 2-alkenylimidazoles: 2-vinylimidazole, 2-isopropenylimidazole, 1-methyl-2-vinylimidazole, 1-methyl-2-isopropenylimidazole, 4,5-dimethyl-2-vinylimidazole, 4(5)-methyl-2-vinylimidazole, 4,5-diphenyl-2-vinylimidazole.

The dehydrogenation reaction is advantageously carried out in the vapor phase in the presence of an inert carrier gas at temperatures of 300°–1000° C., preferably 450°–750° C. It has been found that the optimum reaction conditions are dependent on the nature of the 2-alkylimidazole or 2-alkylimidazoline starting material, the dehydrogenation catalyst used, and the contact time of the vapors with the catalyst. Provided with this recognition those skilled in the art will be able to then determine the optimum conditions by observation. Preferred dehydrogenation catalysts for carrying out the described process include various copper chromites and catalysts comprising of one or more of the metals molybdenum, iron, cobalt, zinc or chromium on nonreducible oxide supports such as alumina or silica. Following the reaction product vapors are condensed and the resultant 2-alkenylimidazole separated from unconverted starting materials and minor side products by conventional methods such as extraction followed by vacuum distillation, ordinary distillation, chromatography and other known procedures.

In carrying out the method of this invention, it is advantageous to add water vapors along with the starting material in order to prolong catalyst life, although such addition of water is not a requirement. When water is employed, it can be used in a molar quantity of from 0-50 times, preferably 5-25 times, the quantity of imidazole or imidazoline fed, with the optimal quantity again being dependent on the nature of the starting material and the catalyst used.

While a number of catalysts are known in the prior art which support the efficient conversion of ethylbenzene to styrene, alkylimidazoles and alkylimidazolines are not converted to the corresponding vinyl compounds under analogous conditions. The presence of the nitrogen atom in the imidazoles and imidazolines requires the use of the unique catalysts and conditions set forth herein.

Among the range of conditions which can successfully be used to carry out the method of this invention are those exemplified by the following.

EXAMPLE 1

2-Ethylimidazole and water, in a molar ratio of one equivalent of imidazole to twenty equivalents of water, are continuously fed into a reactor wherein they are vaporized and their vapors are passed through a catalyst bed comprised of 20 percent chromic oxide ($Cr_2O_3$) and 78 percent cupric oxide (CuO) at a temperature of 695° C. in the presence of an inert gas carrier ($N_2$). An analysis of the condensed product after removal of water shows it to comprise 57 mole percent 2-vinylimidazole and 18 mole percent recovered starting material representing a 69 percent selectivity.

EXAMPLE 2

By following the procedure described in Example 1, but carried out at a temperature of 560° C., there is provided 2-vinylimidazole in 44 percent yield with 85 percent selectivity.

EXAMPLES 3–14

Following the general steps of the procedure of Example 1, various 2-ethylimidazoles are dehydrogenated using different catalysts and reaction conditions. The results are set forth in Table 1.

TABLE I

| Example No. | Starting 2-ethylimidazole | | | | Nominal Catalyst Composition | Temp. °C. | Equiv. Water | Vinylimidazole Yield % | Selectivity, % |
| --- | --- | --- | --- | --- | --- | --- | --- | --- | --- |
| | $R^1$ | $R^2$ | $R^3$ | $R^4$ | | | | | |
| 3 | H | H | H | H | 20% $Cr_2O_3$ + 78% CuO | 600 | 20 | 48 | 90 |
| 4 | H | H | H | H | 20% $Cr_2O_3$ + 78% CuO | 630 | 20 | 59 | 82 |
| 5 | H | H | H | H | 12% $Cr_2O_3$/$Al_2O_3$ | 690 | 20 | 20 | 80 |
| 6 | H | H | H | H | 15% Mo/$Al_2O_3$ | 690 | 20 | 17 | 57 |
| 7 | H | H | H | H | 15% Fe/$Al_2O_3$ | 715 | 20 | 23 | 66 |
| 8 | H | H | H | H | 15% Co/$Al_2O_3$ | 600 | 20 | 32 | 67 |
| 9 | H | H | H | H | 15% Zn/$Al_2O_3$ | 690 | 20 | 38 | 70 |
| 10 | H | H | H | H | 1% $Cr_2O_3$ + 25% CuO + 70% $SiO_2$ | 695 | 20 | 63 | 81 |
| 11 | H | H | H | H | 60% CuO + 30% Zn + 10% $Al_2O_3$ | 675 | 20 | 38 | 48 |
| 12 | H | H | H | H | 12% $Cr_2O_3$/$Al_2O_3$ | 700 | 10 | 40 | 90 |
| 13 | $CH_3$ | H | H | H | 12% $Cr_2O_3$/$Al_2O_3$ | 645 | 0 | 40 | 70 |
| 14 | $CH_3$ | H | H | H | 12% $Cr_2O_3$/$Al_2O_3$ | 645 | 10 | 25 | 35 |

EXAMPLE 15

Following a procedure and conditions similar to Example 1, a 4.7 mole percent aqueous solution of 2-ethylimidazoline is dehydrogenated over a 20 percent $Cr_2O_3$ and; 78 percent CuO catalyst at 618° C. Analysis of the isolated product shows it to comprise 22 mole percent 2-vinylimidazole, 66 mole percent 2-ethylimidazole and 12 mole percent unreacted 2-ethylimidazoline.

EXAMPLE 16

Following conditions identical to those in Example 15 except using a reaction temperature of 650° C., 2-ethylimidazoline is dehydrogenated to provide an isolated product comprising 35 mole percent 2-vinylimidazole and 65 mole percent 2-ethylimidazole. No starting material is recovered.

EXAMPLE 17

Using conditions similar to those of Example 1, a toluene solution of 2-isopropylimidazole is vaporized and the gas stream, in combination with water vapor, is passed through a catalyst bed at 625° C. A ratio of 20 molar parts of water to one part of isopropylimidazole is used and the catalyst is comprised of 20% $Cr_2O_3$ and 78% CuO. A 94% material recovery is obtained and the product is found to consist of 72 mole % 2-isopropenylimidazole and 28% unreacted 2-isopropylimidazole with a melting point of 169.5°–172°. The proton NMR spectrum of 2-isopropenylimidazole contains peaks at 52.19 (3H), 5.15 and 5.60 (2H) and 7.06 (2H), while the $^{13}C$ NMR spectrum exhibits peaks at 20.13, 112.80, 122.56, 134.23 and 148.06. The extrapolated melting point for pure 2-isopropenylimidazole is 186.5° C.

EXAMPLES 18–24

Following the procedure of Example 1, various 2-alkylimidazoles are dehydrogenated. Similar results are achieved. The starting materials are set forth in Table II, below.

TABLE II

| Example No. | Starting 2-alkylimidazole | | | |
| --- | --- | --- | --- | --- |
| | $R^1$ | $R^2$ | $R^3$ | $R^4$ |
| 18 | H | H | H | $CH_3$ |
| 19 | $CH_3$ | H | H | $CH_3$ |
| 20 | H | $CH_3$ | $CH_3$ | H |
| 21 | H | $C_6H_5$ | $C_6H_5$ | H |
| 22 | H | $CH_3$ | H | H |
| 23 | $CH_3$ | $C_6H_5$ | $C_6H_5$ | H |
| 24 | H | $CH_3$ | H | $CH_3$ |

EXAMPLES 25–31

Following the procedure of Example 1, various 2-alkylimidazolines are dehydrogenated with the results achieved being similar thereto. The starting materials are set forth in Table III, below.

TABLE III

| Example No. | Starting 2-alkylimidazolines | | | |
| --- | --- | --- | --- | --- |
| | $R^1$ | $R^2$ | $R^3$ | $R^4$ |
| 25 | H | H | H | H |
| 26 | H | H | H | $CH_3$ |
| 27 | H | $C_6H_5$ | $C_6H_5$ | H |
| 28 | $CH_3$ | H | H | H |
| 29 | $CH_3$ | H | H | H |
| 30 | H | $C_6H_5$ | $C_6H_5$ | $CH_3$ |
| 31 | H | $CH_3$ | $CH_3$ | H |

What is claimed is:
1. A method for preparing a 2-alkenylimidazole having the following structure:

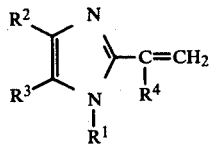

wherein $R^1$ is hydrogen or methyl, $R^2$ and $R^3$ are hydrogen, methyl or phenyl and $R^4$ is hydrogen or methyl comprising selecting a compound selected from the group consisting of 2-alkylimidazole (I) and 2-alkylimidazoline (II) having the following structure:

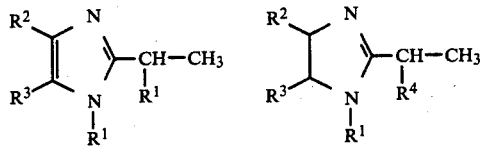

wherein $R^1$, $R^2$, $R^3$ and $R^4$ have the same significance as above and dehydrogenating the compound in the presence of a dehydrogenation catalyst consisting of a supported or unsupported mixture of chromium oxide and copper oxide to yield the 2-alkenylimidazole.

2. The method as claimed in claim 1 further comprising carrying out the dehydrogenation in the presence of an inert carrier gas at a temperature of 300°–1000° C.

3. The method as claimed in claim 2 wherein the temperature is 450°–750° C.

4. The method as claimed in claims 1, 2 or 3 further comprising adding water to the 2-alkylimidazole or 2-alkylimidazoline.

5. The method as claimed in claim 4 wherein the water is present in a molar quantity up to 50 times the quantity of 2-alkylimidazole or 2-alkylimidazoline.

6. The method as claimed in claims 1, or 2 wherein the 2-alkylimidazole (I) is one selected from the group consisting of: 2-ethylimidazole, 2-isopropylimidazole, 1-methyl-2-ethylimidazole, 1-methyl-2-isopropylimidazole, 4,5-dimethyl-2-ethylimidazole 4,5-diphenyl-2-ethylimidazole, 4(5)-methyl-2-ethylimidazole, and 4(5)-methyl-2-isopropylimidazole, and the 2-alkylimidazoline (II) is one selected from the group consisting of: 2-ethylimidazoline, 2-isopropylimidazoline, 1-methyl-2-ethylimidazoline, 1-methyl-2-isopropylimidazoline, and 4,5-dimethyl-2-ethylimidazoline.

7. A method for preparing 2-vinylimidazole comprising heating a compound selected from the group of 2-ethylimidazole and 2-ethylimidazoline in an inert gaseous atmosphere to a temperature in a range of 450°–750° C. in the presence of a catalyst consisting of a supported or unsupported mixture of chromium oxide and copper oxide dehydrogenating the 2-ethylimidazole or 2-ethylimidazoline to form the 2-vinylimidazole and recovering the product 2-vinylimidazole.

8. A method as claimed in claim 7 further comprising adding water in a molar quantity of 5–25 times the 2-ethylimidazole and 2-ethylimidazoline.

9. A method as claimed in claims 7 or 8 wherein the starting materials are added to a flowing stream of the inert gas and passed through a bed of the catalyst.

* * * * *